(12) United States Patent
Taylor et al.

(10) Patent No.: US 10,335,178 B2
(45) Date of Patent: Jul. 2, 2019

(54) ANVIL GRASPER

(71) Applicant: Covidien LP, Mansfield, MA (US)

(72) Inventors: Eric Taylor, Southington, CT (US); Thomas Hessler, Bethel, CT (US); Lou Gonzalez, Raleigh, NC (US)

(73) Assignee: Covidien LP, Mansfield, MA (US)

( * ) Notice: Subject to any disclaimer, the term of this patent is extended or adjusted under 35 U.S.C. 154(b) by 81 days.

(21) Appl. No.: 15/169,919

(22) Filed: Jun. 1, 2016

(65) Prior Publication Data
US 2016/0270808 A1 Sep. 22, 2016

Related U.S. Application Data

(62) Division of application No. 13/785,320, filed on Mar. 5, 2013, now abandoned.

(51) Int. Cl.
*A61B 17/00* (2006.01)
*A61B 17/29* (2006.01)
(Continued)

(52) U.S. Cl.
CPC .............. *A61B 17/29* (2013.01); *A61B 17/11* (2013.01); *A61B 17/282* (2013.01);
(Continued)

(58) Field of Classification Search
CPC ....... A61B 17/29; A61B 17/282; A61B 17/11; A61B 17/1155; A61B 2017/1132; A61B 2017/2936; A61B 2017/2927; A61B 2017/1125; A61B 2017/2926; A61B 2017/2945; A61B 2017/2937; A61B 2017/2939; A61B 17/28; A61B 17/2812; A61B 17/2816; A61B 17/30;
(Continued)

(56) References Cited

U.S. PATENT DOCUMENTS

| 1,918,890 A | 7/1933 | Bacon |
| 2,028,635 A | 1/1936 | Wappler |

(Continued)

FOREIGN PATENT DOCUMENTS

| EP | 0567146 A2 | 10/1993 |
| EP | 0588658 A1 | 3/1994 |

(Continued)

OTHER PUBLICATIONS

European Search Report from EP 14 15 7581 dated May 28, 2014.
(Continued)

*Primary Examiner* — Elizabeth Houston
*Assistant Examiner* — Kankindi Rwego

(57) ABSTRACT

A surgical grasping instrument is provided which includes a body portion having an elongate tubular member extending from the body portion and a jaw assembly movably mounted on a distal end of the elongate tubular member. The jaw assembly includes first and second jaws having arcuate grasping portions for securely grasping a circular surgical stapler anvil shaft. The jaw assembly is mounted on a movable head portion which is movable relative to a longitudinal axis of the elongate tubular member to rotate and articulate the jaw assembly relative to the longitudinal axis to manipulate the anvil within the body of a patient.

17 Claims, 7 Drawing Sheets

(51) Int. Cl.
*A61B 17/28* (2006.01)
*A61B 17/11* (2006.01)
*A61B 17/115* (2006.01)

(52) U.S. Cl.
CPC ... *A61B 17/1155* (2013.01); *A61B 2017/1125* (2013.01); *A61B 2017/1132* (2013.01); *A61B 2017/2926* (2013.01); *A61B 2017/2927* (2013.01); *A61B 2017/2936* (2013.01); *A61B 2017/2945* (2013.01)

(58) Field of Classification Search
CPC .... A61B 2017/2902; A61B 2017/2913; A61B 2017/2919; A61B 2017/2933; A61B 2017/294; A61B 2017/305
See application file for complete search history.

(56) References Cited

U.S. PATENT DOCUMENTS

| | | | |
|---|---|---|---|
| 4,763,669 A | 8/1988 | Jaeger | |
| 5,007,913 A | 4/1991 | Dulebohn et al. | |
| 5,052,402 A * | 10/1991 | Bencini | A61B 10/06 600/564 |
| 5,147,378 A * | 9/1992 | Markham | A61B 17/29 294/100 |
| 5,209,747 A | 5/1993 | Knoepfler | |
| 5,258,006 A | 11/1993 | Rydell et al. | |
| 5,282,826 A | 2/1994 | Quadri | |
| 5,314,424 A | 5/1994 | Nicholas | |
| 5,350,391 A | 9/1994 | Iacovelli | |
| 5,354,312 A | 10/1994 | Brinkerhoff et al. | |
| 5,443,479 A * | 8/1995 | Bressi, Jr. | A61B 17/1114 606/205 |
| 5,456,684 A | 10/1995 | Schmidt et al. | |
| 5,522,839 A * | 6/1996 | Pilling | A61B 17/0218 600/204 |
| 5,575,799 A | 11/1996 | Bolanos et al. | |
| 5,603,723 A | 2/1997 | Aranyi et al. | |
| 5,618,294 A | 4/1997 | Aust et al. | |
| 5,636,639 A * | 6/1997 | Turturro | A61B 10/0266 600/564 |
| 5,637,110 A | 6/1997 | Pennybacker et al. | |
| 5,662,662 A | 9/1997 | Bishop et al. | |
| 5,797,939 A * | 8/1998 | Yoon | A61B 17/122 606/167 |
| 5,817,119 A | 10/1998 | Klieman et al. | |
| 5,827,323 A | 10/1998 | Klieman et al. | |
| 6,592,572 B1 | 7/2003 | Suzuta | |
| 6,673,092 B1 | 1/2004 | Bacher | |
| 7,083,620 B2 | 8/2006 | Jahns et al. | |
| 7,487,780 B2 | 2/2009 | Hooven | |
| 7,540,872 B2 | 6/2009 | Schechter et al. | |
| 7,605,559 B2 | 10/2009 | Messerly et al. | |
| 2006/0020241 A1 | 1/2006 | Piskun et al. | |
| 2006/0155326 A1 | 7/2006 | Aranyi | |
| 2007/0276430 A1 | 11/2007 | Lee et al. | |
| 2008/0027476 A1 | 1/2008 | Piskun | |
| 2010/0016852 A1 | 1/2010 | Manzo et al. | |
| 2010/0057121 A1 | 3/2010 | Piskun et al. | |
| 2011/0060376 A1 | 3/2011 | Li | |
| 2011/0106078 A1 | 5/2011 | Mueller | |
| 2012/0065665 A1 | 3/2012 | Williams et al. | |
| 2012/0172924 A1 | 7/2012 | Allen, IV | |
| 2012/0303025 A1 * | 11/2012 | Garrison | A61B 17/29 606/51 |

FOREIGN PATENT DOCUMENTS

| | | |
|---|---|---|
| EP | 0592244 A2 | 4/1994 |
| EP | 1637086 A1 | 3/2006 |
| EP | 1870043 A2 | 12/2007 |
| EP | 1923009 A2 | 5/2008 |
| WO | 93/14801 | 8/1993 |
| WO | 02/07611 | 1/2002 |
| WO | 20050072663 A1 | 8/2005 |
| WO | 2006/113216 A2 | 10/2006 |

OTHER PUBLICATIONS

European Search Report dated Mar. 24, 2010 from EP Application No. 09 252 160.8 (13 pgs.).
European Examination Report issued in corresponding European Application No. 14157581.1 dated Jul. 13, 2017.

* cited by examiner

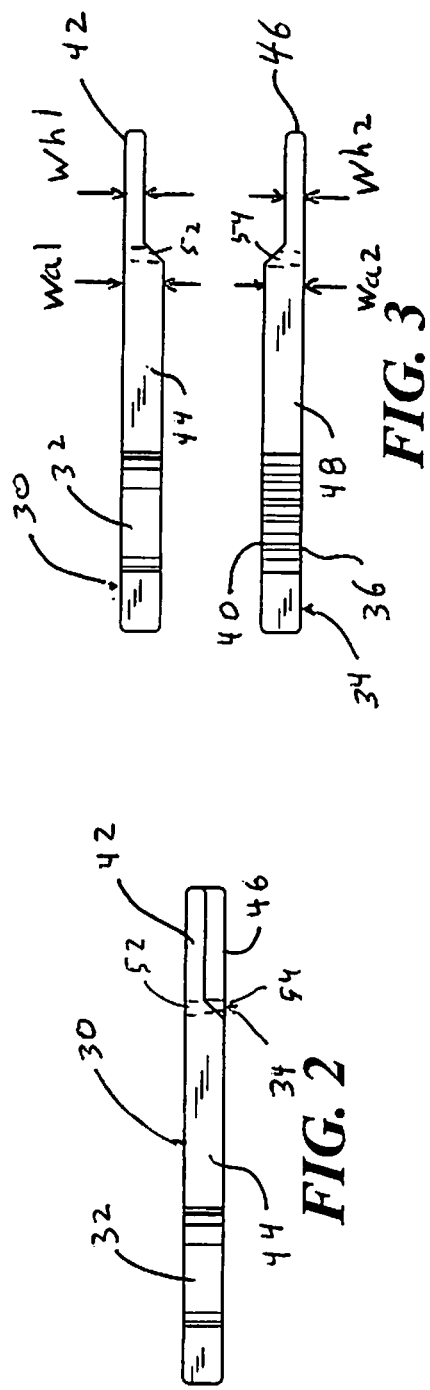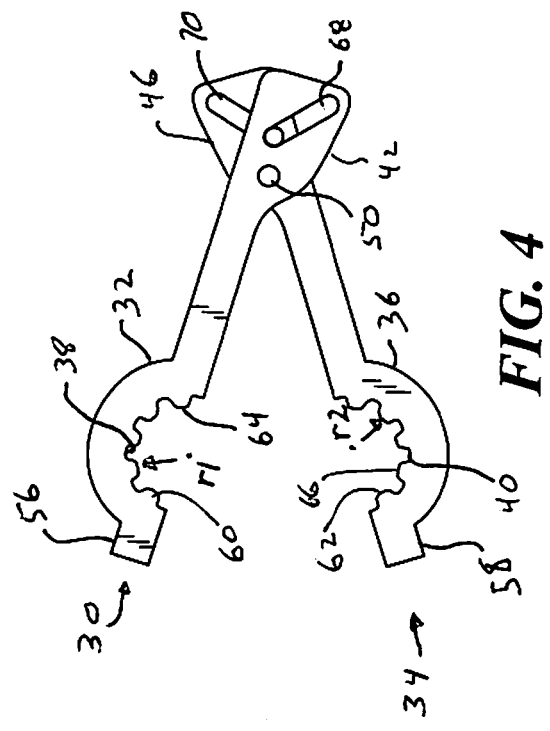

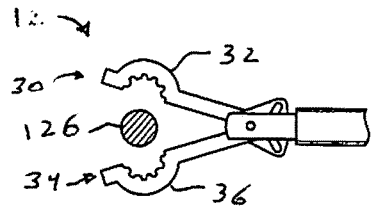
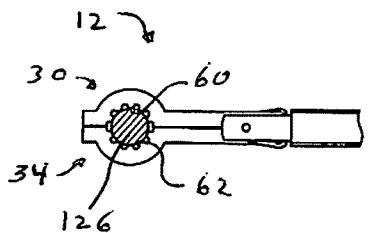
FIG. 12  FIG. 13
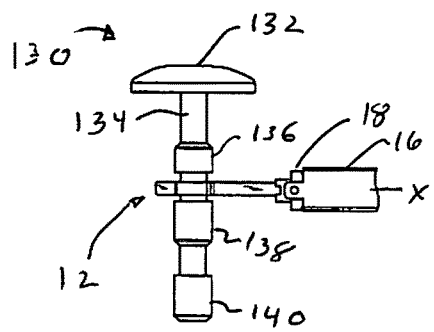
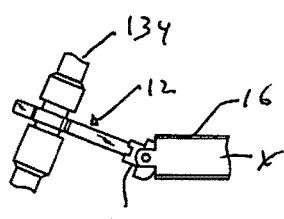
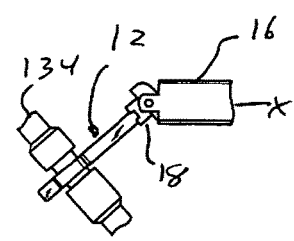
FIG. 14  FIG. 15  FIG. 16
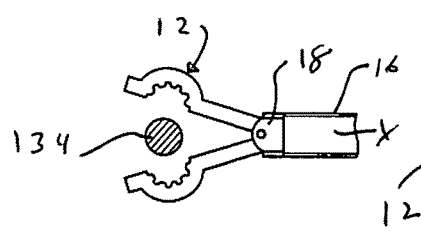
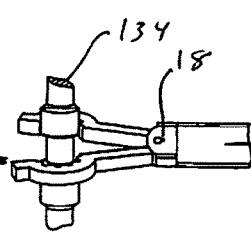
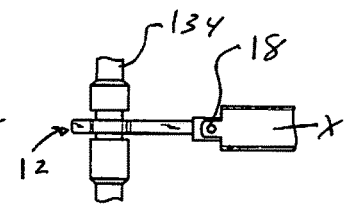
FIG. 17  FIG. 18  FIG. 19

ANVIL GRASPER

CROSS-REFERENCE TO RELATED APPLICATIONS

The present application is a Divisional Application which claims the benefit of and priority to U.S. patent application Ser. No. 13/785,320, filed on Mar. 5, 2013, the entire disclosure of which is hereby incorporated by reference herein.

BACKGROUND

1. Technical Field

The present disclosure relates to a surgical grasping instrument. More particularly, the present disclosure relates to a surgical grasping instrument having a jaw assembly with arcuate gripping portions to securely grasp a cylindrical surgical object.

2. Background of Related Art

During certain surgical procedures, it is often necessary to remove damaged section of tubular tissue sections and reconnect the healthy free ends. This is often accomplished with the use of a circular surgical stapler. The circular surgical stapler has a removable anvil assembly which is positioned within one of the free ends of the healthy tubular tissue. The anvil assembly includes a staple clinching anvil head or cap and an anvil shaft extending from the anvil cap.

The circular surgical stapler is positioned within the other free end of healthy tubular tissue and the anvil shaft is connected to the stapler. The anvil cap is drawn adjacent to a staple containing head of the stapler and the stapler is fired to form a circular ring of staples reconnecting the healthy free ends of the tubular tissues. Thereafter, a circular knife blade cores away any tissue remaining radially inwardly of the ring of staples and the circular surgical stapler including the anvil assembly is removed as a single unit.

In order to position the anvil assembly within the body of a patient and into a free end of tubular tissue, the anvil assembly is grasped and manipulated into position by a grasping instrument at the anvil shaft. Grasping instruments have a jaw assembly including first and second jaws with flat grasping surfaces. When engaged by the flat grasping surfaces of the jaw assembly, the anvil shaft can skew sideways, slip or slide relative to the flat grasping surfaces of the jaws making it difficult to grasp the anvil assembly, manipulate it into position and reattach it to the circular stapler. The round anvil can also easily drop out of the flat jaws of the grasping instrument. This quite often extends the time of the surgical operation and leads to increased frustration levels for the surgeon.

Therefore, a need exists for a jaw assembly configured to firmly grasp the round shaft of a circular surgical anvil assembly. There also exists a need for a surgical grasping instrument capable of firmly grasping the round shaft of a circular surgical anvil assembly and manipulate it into position to be reconnected to a circular surgical stapler.

SUMMARY

There is disclosed a jaw assembly for use with a surgical grasping instrument. The jaw assembly generally includes a first jaw having a first arcuate gripping portion and a first arm extending from the first arcuate gripping portion and a second jaw having a second gripping portion and a second arm extending from the second gripping portion. The first and second arms are movably connected such that the first arcuate gripping portion and second gripping portion are spaced apart in the open condition.

In one embodiment, the second gripping portion is also arcuate. In a specific embodiment, at least one of the first and second arcuate gripping portions is semi-cylindrical. In a more specific embodiment both the first and second arcuate gripping portions are semi-cylindrical.

The first arcuate gripping portion includes radially inwardly directed teeth to increase friction between the first arcuate gripping portion and a cylindrical object to be grasped. The radially inwardly directed teeth terminate in flats to further increase the frictional contact with the object. The flat ends of the jaws do not necessarily touch, but they are very close.

The first and second arms are movably connected by a pivot point such that the first and second jaws are movable from an open condition with the first arcuate gripping portion and second gripping portion spaced apart to a closed condition with the first arcuate gripping portion and the second gripping portion in close cooperative alignment to capture the object.

At least one of the first and second arms includes a base portion having an angled drive slot. In a specific embodiment, both the first and second arms include base portions having angled drive slots.

In one embodiment, the first and second arms are movably connected by a flexible member. In a specific embodiment, the flexible member is a living hinge. In this embodiment, the first and second jaws are integrally formed.

There is also disclosed a surgical grasping instrument for gripping a cylindrical object which generally includes a body portion having a stationary handle and a pivotal handle movably mounted on the body portion. An elongate tubular member extends distally from the body portion and a jaw assembly is movably mounted relative to a distal end of the elongate tubular member. The jaw assembly includes a first jaw having a first arcuate gripping portion and a second jaw having a second arcuate gripping portion. The first and second arcuate gripping portions are movable between an open condition spaced apart to a closed condition in close cooperative alignment. The first and second arcuate gripping portions are semi-cylindrical and include radially inwardly extending teeth along inner surfaces thereof to increase the grip on the object. The jaw assembly is connected to the distal end of the elongate tubular member by a movable head portion. The head portion is movable to articulate and rotate the jaw assembly relative to a longitudinal axis of the elongate tubular member.

There is further disclosed a method of gripping a cylindrical surgical object by providing a surgical instrument including a first jaw having a first arcuate gripping portion and a second jaw having a second arcuate gripping portion. The first jaw is positioned relative to the second jaw such that the concavities of the first and second arcuate gripping portions face each other in an open condition and the first and second arcuate gripping portions are positioned about a cylindrical object to be grasped. The surgical instrument is then actuated to move the first and second gripping portions to a closed condition in contact with the cylindrical object. In a specific version of the disclosed method, the first and second gripping portions contact the cylindrical object with radially inwardly extending teeth to enhance the grip on the object.

DESCRIPTION OF THE DRAWINGS

Various embodiments of the presently disclosed anvil grasper are disclosed herein with reference to the drawings, wherein:

FIG. 2 is a top plan view of the anvil grasping jaws of FIG. 1;

FIG. 3 is a top plan view, with parts separated, of the anvil grasping jaws of FIG. 1;

FIG. 4 is a side view of the pair of anvil grasping jaws;

FIG. 12 is a side view, partially shown in section, of the distal end of the surgical grasping instrument of FIG. 1 with the pair of anvil grasping jaws positioned about a shaft of a surgical stapler anvil;

FIG. 13 is a side view similar to FIG. 12 with the pair of anvil grasping jaws closed about the shaft of the surgical stapler anvil;

FIG. 14 is a top plan view of the distal end of the surgical grasping instrument of FIG. 1 holding the surgical stapler anvil;

FIG. 15 is a top plan view similar to FIG. 14 with the surgical stapler anvil articulated relative to the outer tubular member in a first direction;

FIG. 16 is a top plan view similar to FIG. 15 with the surgical stapler anvil articulated in a second direction;

FIG. 17 is a side plan view of the distal end of the surgical grasping instrument of FIG. 1 with the pair of anvil grasping jaws positioned about the shaft of the surgical stapler anvil;

FIG. 18 is a side plan view similar to FIG. 17 with the surgical stapler anvil rotated relative to a long axis of the outer tubular member;

FIG. 19 is a side plan view similar to FIG. 18 with the surgical stapler anvil rotated 90° relative to the position of FIG. 17;

DETAILED DESCRIPTION OF EMBODIMENTS

Embodiments of the presently disclosed surgical grasping instrument incorporating a pair of anvil grasping jaws will now be described in detail with reference to the drawings wherein like numerals designate identical or corresponding elements in each of the several views. As is common in the art, the term 'proximal" refers to that part or component closer to the user or operator, i.e. surgeon or physician, while the term "distal" refers to that part or component further away from the user.

Figure 1:
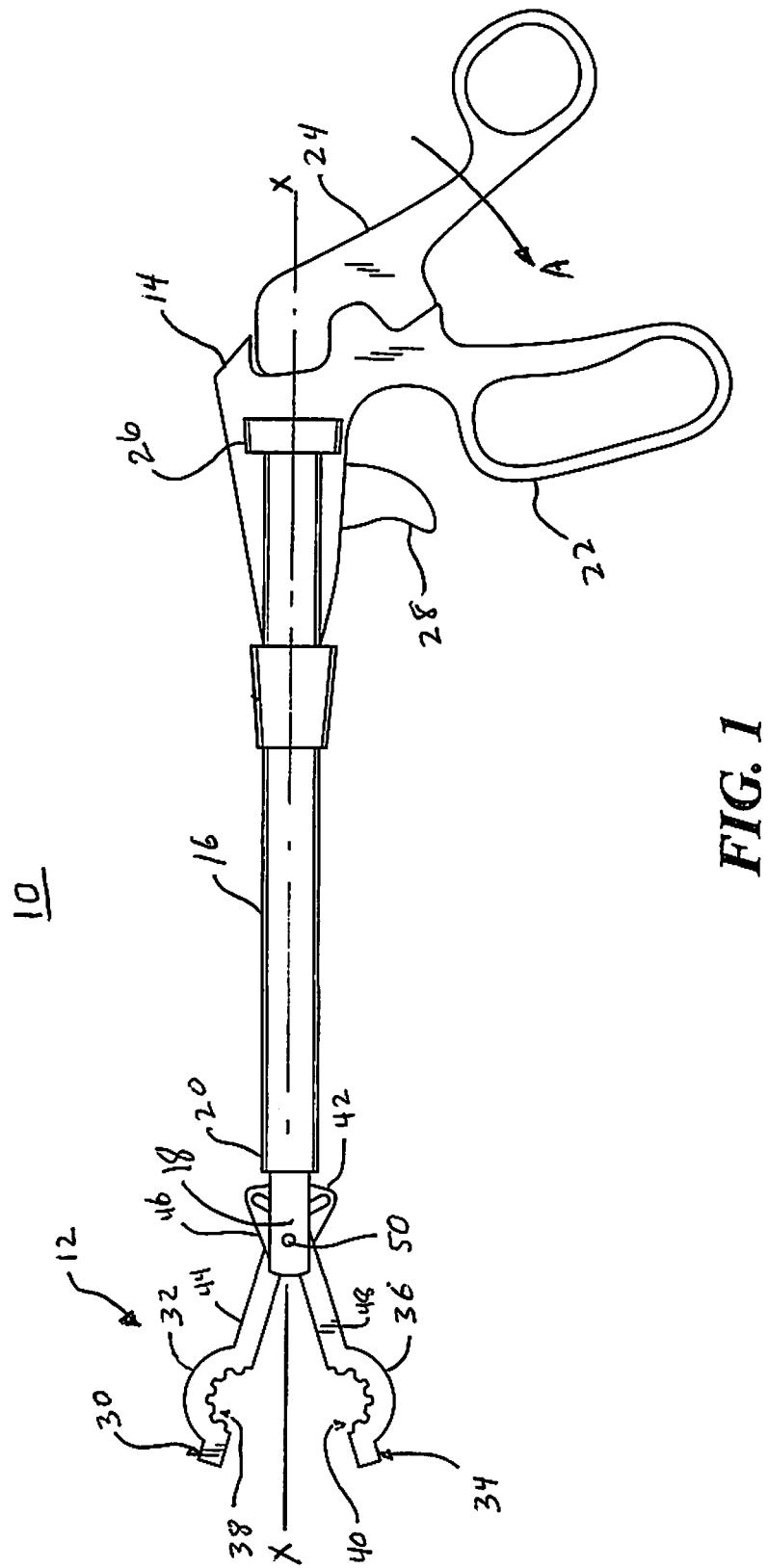
FIG. 1 is a surgical grasping instrument incorporating one embodiment of a pair of anvil grasping jaws.

Referring initially to FIG. 1, there is disclosed a surgical grasping instrument 10 incorporating one embodiment of a pair of anvil shaft grasping jaws or grasping jaw assembly 12 for use in grasping and manipulating a shaft of a circular surgical stapler anvil (see FIG. 14) or other cylindrical object in a manner described in more detail hereinbelow. Surgical grasping instrument 10 generally includes a body portion 14 having an elongate tubular member 16 extending distally from body portion 14. A movable jaw mount or head portion 18 is movably mounted on a distal end 20 of elongate tubular member 16 and is provided to rotate and articulate grasping jaw assembly 12 relative to a longitudinal axis x-x of elongate tubular member 16.

Body portion 14 includes a stationary handle 22 and a pivotal handle 24 movably mounted on stationary handle 22. Pivotal handle 24 is operable to open and close grasping jaw assembly 12 in a manner described hereinbelow. Body portion 14 additionally includes a rotation knob 26 to rotate head portion 18, and thus grasping jaw assembly 12, relative to longitudinal axis x-x and an articulation trigger 28 to angulate or articulate head portion 18 relative to longitudinal axis x-x to better position grasping jaw assembly 12 and manipulate structure retained in grasping jaw assembly 12. An example of a surgical instrument having rotational and articulation capabilities is described in U.S. Pat. No. 5,314,424, the entire disclosure of which is hereby incorporated by reference herein.

Grasping jaw assembly 12 generally includes a first jaw 30 having a first curved or arcuate gripping portion 32 and a second jaw 34 having a second curved or arcuate gripping portion 36. First and second gripping portions 32 and 36 include respective first and second inner gripping surfaces 38 and 40, the concavities of which face inwardly towards each other. First jaw 30 further includes a first proximal base portion 42 and a first arm 44 extending between first base portion 42 and first gripping portion 32. Similarly, second jaw 34 includes a second proximal base portion 46 and a second arm 48 extending between second proximal base portion 46 and second gripping portion 36. First and second jaws 30 and 34 are pivotally mounted to head portion by a pivot pin 50. Each of the first and second jaws 30 and 34 desirably have a flat distal end that engages one another. First jaw 30 has flat distal end 30a and second jaw 34 has flat distal end 34a.

Referring now to FIGS. 2 and 3, pivot pin 50 extends through pin holes 52 and 54 formed through first and second head portions 42 and 46. First and second head portions 42 and 46 of first and second jaws 30 and 34 overlap each other and have reduced thicknesses relative to the remainder of their respective jaws. With specific reference to FIG. 3, first head portion 42 has a thickness Wh1 which is less than a thickness Wa1 of first arm 44 of first jaw 30. Likewise, second head portion 46 has a thickness Wh2 which is less than a thickness Wa2 of second arm 48 of second jaw 34.

Figure 5:
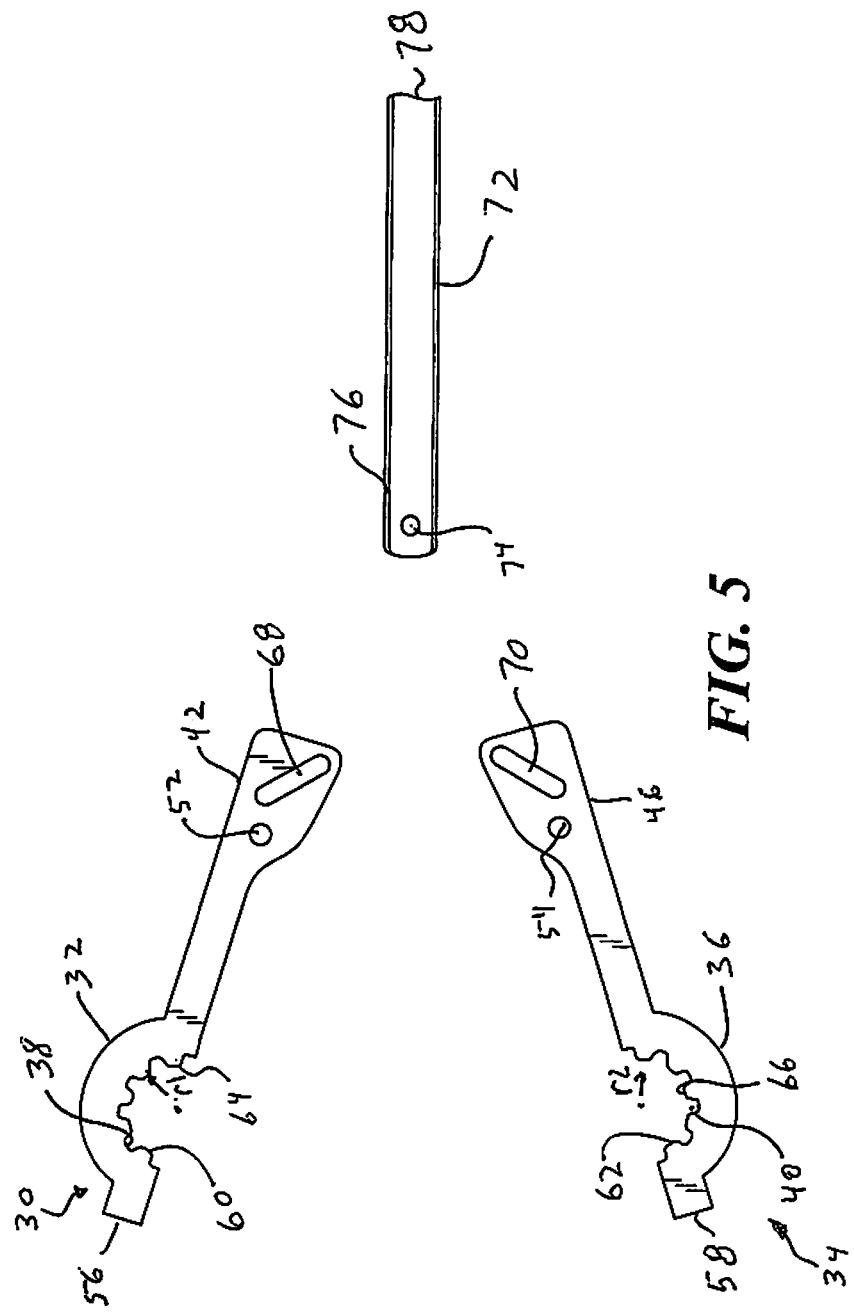
FIG. 5 is a side view, with parts separated, of the pair of anvil grasping jaws and a drive rod.

With reference to FIGS. 4 and 5, longitudinally extending distal tips 56 and 58 extend distally from first and second gripping portions 32 and 36 to better guide grasping jaw assembly into engagement with a surgical stapler anvil. First and second inner surfaces 38 and 40 of first and second gripping portions 32 and 326 are semi-circular having constant radii r1 and r2, respectively. While first and second inner surfaces 38 and 40 are disclosed as having constant radii, it is also contemplated that one or both surfaces may have varying radii depending on the configuration of the anvil shaft to be grasped.

In order to better grasp a cylindrical object, such as, for example an anvil shaft, first and second inner surfaces 38 and 40 of first and second gripping portions 32 and 36 of first and second jaws 30 and 34 are treated or include structure to increase friction between first and second inner surfaces 38 and 40 and an anvil shaft. In this embodiment, first and second inner surfaces 38 and 40 include respective radially inwardly directed teeth 60 and 62. Teeth 60 and 62 extend cross-wise across first and second inner surfaces 38 and 40 (See FIG. 3). In order to avoid damage to an anvil shaft grasped, and provide a greater contact surface, teeth 60 and 62 are provided with relatively flat or rounded ends 64 and 66.

First and second jaws 30 and 34 are movable between an open or spaced apart condition and a closed gripping or adjacent condition wherein first and second jaws 30 and 34 are in close cooperative alignment to grasp structure. In order to move first and second jaws 30 and 34 between the open and closed conditions, first and second proximal base portions 42 and 46 of first and second jaws 30 and 34 include respective angled drive slots 68 and 70.

Referring to FIG. 5, the anvil grasper includes a drive rod 72 for moving first and second jaws 30 and 34 between the open and closed conditions in response to movement of pivot handle 24 (FIG. 1). Specifically, angled drive slots 68 and 70 receive a cross-wise extending drive pin 74 provided on a distal end 76 of drive rod 72. A proximal end 78 of drive rod 72 is operably connected to pivot handle 24. Movement of drive pin 74 proximally within drive slots 68 and 70 cams first and second jaws 30 and 34 to the closed condition as discussed in more detail hereinbelow. In any of the embodiments disclosed herein, the drive rod 72 can be moved distally, rather than proximally, to close the first and second jaws, and the drive slots can be oriented accordingly.

First and second jaws 30 and 34 may be formed from a variety of materials including metals, such as, for example, titanium, stainless steel, etc. Alternatively, first and second jaws 30 and 34 may be formed from other materials, such as, polymeric materials, ceramics, etc. Methods of formation may include forging, molding, machining, etc.

Referring now to FIGS. 1 and 6-8, and initially with regard to FIG. 1, the operation of grasping jaw assembly 12 will now be described. Initially first and second jaws 30 and 34 are in an open condition spaced apart from each other to receive structure. Pivot handle 24 is in an initial position spaced from stationary handle 22.

Figure 6:
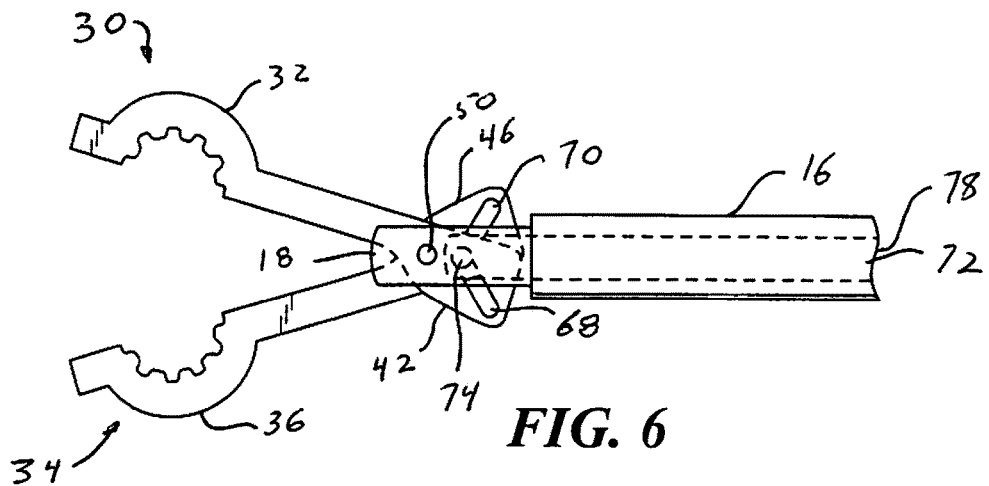
FIG. 6 is a side view of a distal end of the surgical grasping instrument of FIG. 1 with the pair of surgical grasping jaws in an open position.

Turning to FIG. 6, and while not specifically shown, an internal bias spring maintains grasping jaw assembly 12 in the open condition by exerting a distal bias to drive rod 72. In the initial or open condition, drive pin 74 is in a distal most position within drive slots 68 and 70 formed in first and second proximal base portions 42 and 46 of respective first and second jaws 30 and 34.

Figure 7:
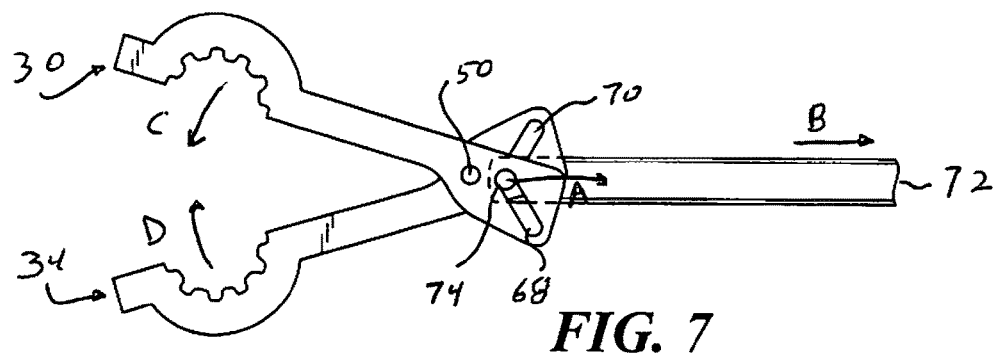
FIG. 7 is a view similar to FIG. 6 with an outer tubular member of the surgical grasping instrument removed.

With reference to FIGS. 1 and 7, to actuate movement of first and second jaws 30 and 34, pivotal handle 24 is moved in the direction of arrow A toward stationary handle 22 (FIG. 1). As pivotal handle 24 is swung toward stationary handle 22, pivotal handle 24 draws proximal end 78, and thus drive rod 72, proximally in the direction of arrow B within elongate tubular member 16 against the bias of the spring. Proximal movement of drive rod 72 draws drive pin 74 proximally within drive slots 68 and 70 of first and second jaws 30 and 34 camming or forcing first and second jaws 30 and 34 to rotate inwardly in the directions of arrows C and D about pivot pin 50.

Figure 8:
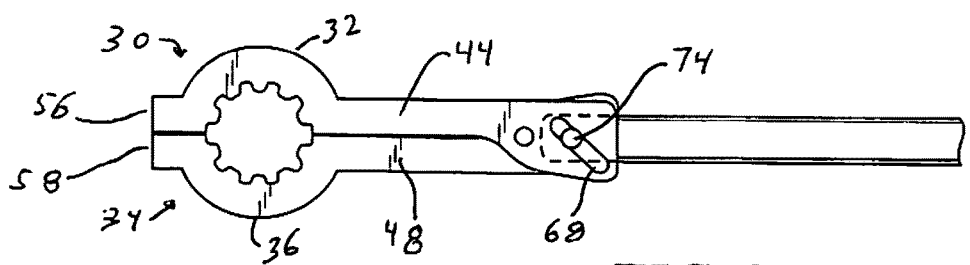
FIG. 8 is a side view similar to FIG. 7 with the pair of anvil grasping jaws in a closed position.

Referring to FIG. 8, as drive pin 74 of drive rod 72 is drawn to its proximal most position within drive slots 68 and 70, first and second jaws 30 and 34 are brought to the closed condition with first and second distal tips 56 and 58 in abutting relation to cause first and second gripping portions 32 and 36 to close about a structure to be grasped. When the jaws close, the flat distal ends 30*a* and 34*a* touch and engage one another without interfering with the shaft of the anvil. Thus, the first jaw and second jaw substantially enclose the shaft of the anvil. Even if the ends do not touch, the shaft is substantially enclosed.

Figure 9:
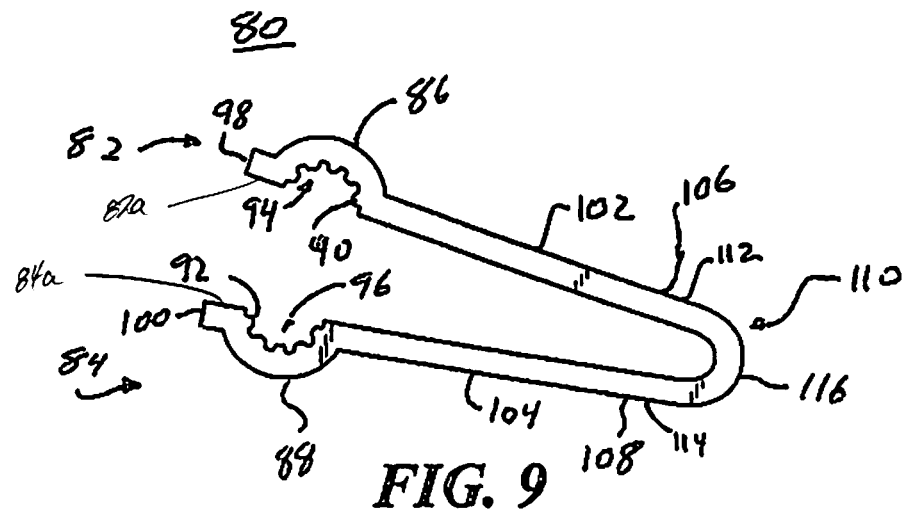
FIG. 9 is a side view of an alternate embodiment of a pair of anvil grasping jaws.
Figure 10:
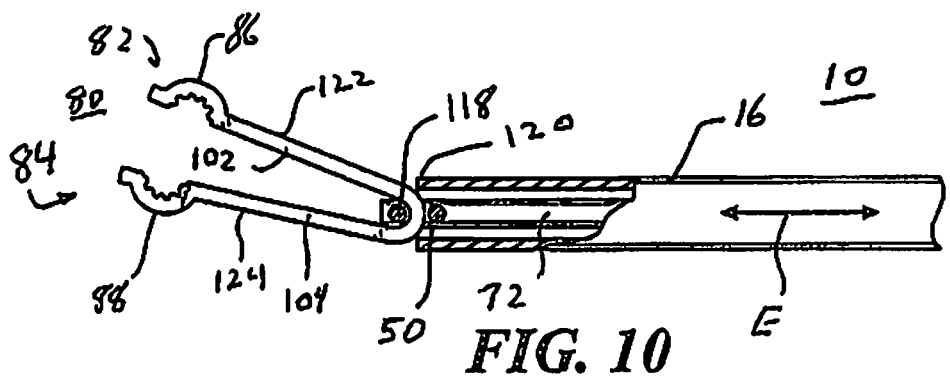
FIG. 10 is a perspective view, partially shown in section, of a distal end of a surgical grasping instrument incorporating the pair of anvil grasping jaws of FIG. 9.
Figure 11:
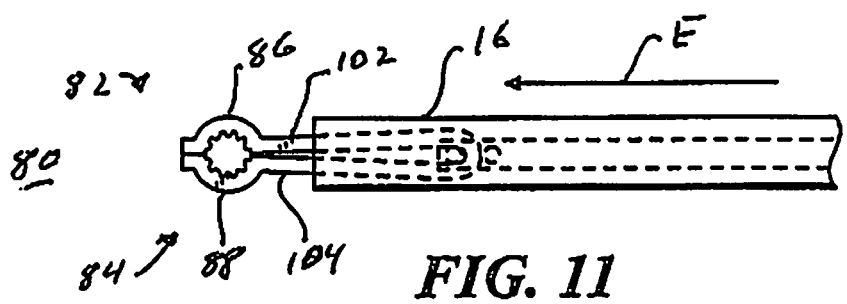
FIG. 11 is a side view of the distal end of the surgical grasping instrument of FIG. 10 with the pair of anvil grasping jaws moved to a closed position.

Referring to FIGS. 9-11, and initially with regard to FIG. 9, there is disclosed an alternative grasping jaw assembly 80 for use with surgical grasping instrument 10. Grasping jaw assembly 80 includes first and second jaws 82 and 84 which are substantially similar to first and second jaws 30 and 36 described hereinabove including respective first and second arcuate gripping portions 86 and 88. First and second gripping portions include teeth 90 and 92 formed along first and second inner surfaces 94 and 96 of first and second jaws 82 and 84 respectively. Similar to jaws 30 and 34 described hereinabove, first and second jaws 82 and 84 include distal tips 98 and 100 extending distally from first and second gripping portions 86 and 88 and first and second arms 102 and 103 extending proximally from first and second gripping portions 86 and 88, respectively.

In contrast to first and second jaws 30 and 36, which are initially biased apart by a spring (not shown) acting on drive rod 72 (FIG. 6), proximal ends 106 and 108 of respective first and second jaws 82 and 84 are connected to a flexible connector or living hinge 110 which maintains first and second jaws 82 and 84 biased to the open condition spaced apart from each other. Specifically, living hinge 110 includes first and second ends 112 and 114 which are connected to proximal ends 106 and 108 of first and second arms 102 and 104 of first and second jaws 82 and 84. First and second ends 112 and 114 of living hinge 110 are integrally formed with proximal ends 106 and 108 by molding, machining, forging, etc. or, alternatively, may be affixed thereto by known methods such as, for example, welding, gluing, etc. First and second jaws 82 and 84 also have flat distal ends 82*a* and 84*a*, as discussed above.

First and second ends 112 and 114 of living hinge 110 extend from a curved, flexible center portion 116. Curved center portion 116 may be formed from a variety of flexible materials such as, for example, stainless or spring steel, polymeric materials, etc. and need not necessarily be formed from the same material as first and second jaws 82 and 84. Curved center portion 116 biases first and second jaws 82 and 84 of jaw assembly 80 to an initial open condition.

Referring now to FIGS. 10 and 11, the operation of jaw assembly 80 will now be described. In this embodiment, drive rod 72 is fixed stationary to stationary handle 22 and elongate tubular member 16 is longitudinally movable relative to stationary handle 22 in response to movement of handle 24. This is accomplished through various methods known in the art, for example, the closure mechanism associated with linear surgical stapling devices wherein an outer member is longitudinally movable to cam an anvil closed against a staple cartridge. Curved center portion 116 is positioned against drive pin 50 which remains stationary. Curved center portion 116 is held in place by a retention pin 118 on drive rod 72 as shown. It should be noted that, in the biased open condition, the concavities of first and second arcuate gripping portions 96 and 94 face each other.

Initially, first and second jaws 82 and 84 are in an open condition space apart from each other. Upon actuation of pivotal handle 24, elongate tubular member 16 is driven distally relative to drive rod 72 in the direction of arrow E. As elongate tubular member 16 travels distally, a distal end 120 of elongate tubular member 16 rides up on and cams against outer surfaces 122 and 124 of first and second arms 102 and 102 thereby camming first and second jaws 82 and 84 together to capture a cylindrical structure between first and second curved gripping portions 94 and 96. The first and second jaws 82 and 84 substantially surround the shaft of the anvil.

Referring now to FIGS. 1 and 12-19, and initially with regard to FIGS. 1, 12 and 13, the use of surgical grasping instrument 10 will now be described. Initially, pivotal handle 24 is in a proximal most position spaced from stationary handle 22 (FIG. 1). First and second jaws 30 and 34 of grasping jaw assembly 12 are in the open condition spaced apart from each other. As shown, in the initial or open condition, the concavities of first and second arcuate gripping portions 32 and 36 face inwardly toward each other.

Surgical grasping instrument 10 is manipulated to position first and second jaws 30 and 34 about an object to be grasped, such as, for example, cylindrical object 126 (FIG. 12). Thereafter, pivotal handle 24 is moved in the direction of arrow A toward stationary handle 22 (FIG. 1) thereby forcing first and second jaws 30 and 34 to move to the closed condition about cylindrical object 126.

Referring to FIGS. 14-16, surgical grasping instrument 10 is specifically designed to grasp and manipulate a surgical stapler anvil, such as, for example, circular surgical stapler anvil assembly 130. Anvil assembly 130 generally includes an anvil head 132 for clinching surgical staples (not shown) and a cylindrical anvil shaft 134 extending from anvil head 132. Anvil shaft 134 may include one or more circumferential, enlarged diameter bosses 136, 138 and 140 for engagement with a circular surgical stapler.

Anvil assembly 130 is grasped in the manner described herein above with regard to cylindrical object 126. Should a surgeon desire to move anvil assembly 130 side to side, articulation trigger 28 on stationary handle 22 (FIG. 1) is operated to move head portion 18, and thus grasping jaw assembly 12 (FIGS. 15 and 16) relative to longitudinal axis X of elongate tubular member 16. Trigger 28 is really the release grasp trigger, since the jaws will lock when clamped down. There is no articulation knob shown, but it would be placed further back on the handle.

Referring to FIGS. 17-18, anvil assembly 130 can be rotated about longitudinal axis X by rotating rotation knob 26 on stationary handle 22 (FIG. 10). Rotation of rotation knob 26 rotates head portion 18, and thus grasping assembly 12, about longitudinal axis X to thereby rotate anvil assembly 130 to a desired position.

Figure 20:
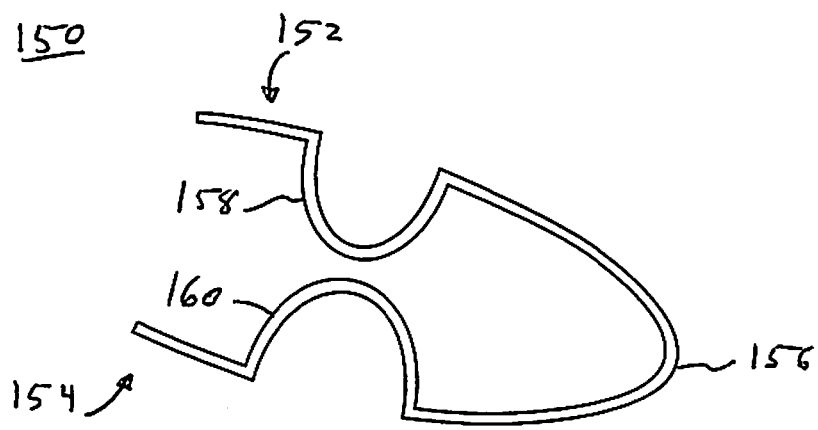
FIG. 20 is a side plan view of a further alternate embodiment of a pair of anvil grasping jaws.
Figure 21:
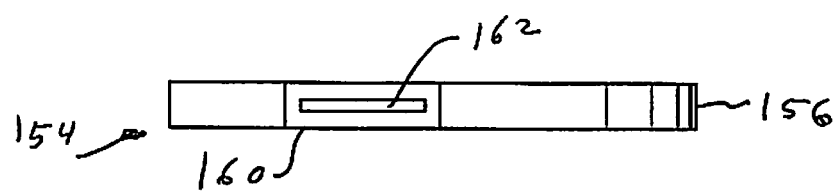
FIG. 21 is a bottom plan view of the anvil grasping jaws of FIG. 20.
Figure 22:
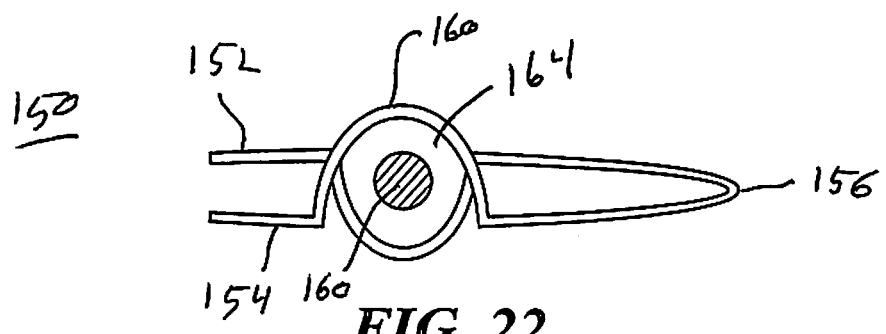
FIG. 22 is a side plan view, partially shown in section, of the embodiment of FIG. 20 positioned about the shaft of the surgical stapler anvil.

Referring now to FIGS. 20-22, there is disclosed a further embodiment of a grasping jaw assembly 150 for use with surgical grasping instrument 10. Grasping jaws assembly 150 is similar to grasping jaw assembly 80 and generally includes first and second jaws 152 and 154 connected by a living hinge 156. First and second jaws 152 and 154 include respective first and second arcuate gripping portions 158 and 160. However, unlike the prior embodiments, in the open or biased condition the concavities of first and second arcuate gripping portions 158 and 160 face outwardly away from each other (FIG. 20) rather than inwardly toward each other.

As best shown in FIG. 21, in order to form a circle to capture a cylindrical object, second jaw 154 includes a longitudinally extending slot 162 formed through second gripping portion 160. First gripping portion 158 is sized to pass through slot 162 in second gripping portion 160.

Referring to FIG. 22, in use, first and second jaws 152 and 154 are initially compressed together causing first gripping portion 158 to pass through slot 162 in second gripping portion 160 thereby forming a space 164. Grasping jaw assembly 150 is manipulated such that it is positioned about a cylindrical object or anvil shaft 166. Thereafter, compression is reduced on first and second jaws 152 and 154 causing first and second gripping portions 158 and 160 to move outwardly due to the bias of living hinge 156 and grasp anvil shaft 166.

Thus, the disclosed grasping jaw assemblies are able to grasp, rotate and articulate a surgical anvil shaft without the shaft sliding out of the jaws of the jaw assemblies.

It will be understood that various modifications may be made to the embodiments disclosed herein. For example, the disclosed gripping portions may be of other shapes, such as, for example, semi oval, rectangular, etc to prevent the grasped object from skewing from side to side. Further, the disclosed jaw assemblies may include only one arcuate gripping portion on a single jaw. Additionally, other method of enhancing the friction of the grasping portions against a grasped object may be provided, such as, for example, cross-hatching, stippling, etc. the inner surfaces. Therefore, the above description should not be construed as limiting, but merely as exemplifications of particular embodiments. Those skilled in the art will envision other modifications within the scope and spirit of the claims appended hereto.

What is claimed is:

1. A jaw assembly for use with a surgical grasping instrument comprising:
   a drive rod including a drive pin and a retention pin disposed along a longitudinal axis defined by the drive rod;
   a first jaw having a first arcuate gripping portion and a first arm extending from the first arcuate gripping portion;
   a second jaw having a second arcuate gripping portion and a second arm extending from the second arcuate gripping portion; and
   a living hinge interconnecting the first and second arms of the respective first and second jaws, the living hinge held in place between the drive pin and the retention pin such that the living hinge and the drive rod are movable as a single construct, the first and second jaws transitionable between an open position in which the first and second arcuate gripping portions are spaced apart and a closed position in which the first and second arcuate gripping portions are in close cooperative alignment, wherein each arm of the first and second arms includes an engaging portion configured to be cammed against an elongate tubular member of the surgical grasping instrument to transition the first and second jaws between the open and closed positions, the engaging portions of the respective first and second arms being coplanar with remaining portions of the respective first and second arms.

2. The jaw assembly according to claim 1, wherein at least one of the first or second arcuate gripping portions is semi-cylindrical.

3. The jaw assembly according to claim 1, wherein the first and second arms extend linearly from the respective first and second arcuate gripping portions.

4. The jaw assembly according to claim 1, wherein at least one of the first or second arcuate gripping portions includes teeth extending radially inward.

5. The jaw assembly according to claim 1, wherein the living hinge and the first and second jaws are integrally formed.

6. The jaw assembly according to claim 1, wherein the living hinge includes a curved center portion formed of a flexible material.

7. The jaw assembly according to claim 1, wherein the first and second jaws are biased toward the open position.

8. The jaw assembly according to claim 1, wherein concavities of the first and second arcuate gripping portions of the respective first and second jaws face each other when the first and second jaws are in the closed position.

9. The jaw assembly according to claim 1, wherein at least one of the first or second arms has a uniform thickness.

10. The jaw assembly according to claim 1, wherein the longitudinal axis of the drive rod is aligned with a central longitudinal axis defined by the elongate tubular member of the surgical grasping instrument.

11. The jaw assembly according to claim 1, wherein the first jaw includes a first alignment portion extending distally from the first arcuate gripping portion, the first alignment portion being coplanar with the first arm.

12. The jaw assembly according to claim 11, wherein the second jaw includes a second alignment portion extending distally from the second arcuate gripping portion, the first and second alignment portions are in surface contact when the first and second jaws are in the closed position.

13. A surgical grasping instrument for gripping a cylindrical object comprising:
an elongate tubular member defining a longitudinal axis; and
a jaw assembly supported adjacent a distal end of the elongate tubular member, the jaw assembly including:
a drive rod disposed in the elongate tubular member, the drive rod including a drive pin and a retention pin disposed along the longitudinal axis of the elongate tubular member;
a first jaw having a first arcuate gripping portion and a first arm extending proximally from the first arcuate gripping portion, the first arm including a first engaging portion;
a second jaw having a second arcuate gripping portion and a second arm extending proximally from the second arcuate gripping portion, the second arm including a second engaging portion; and
a living hinge interconnecting the first and second jaws, the living hinge securely interposed between the drive pin and the retention pin of the drive rod such that the first and second jaws are movable with the drive rod as a single construct, wherein the elongate tubular member is transitionable between a proximal position in which the first and second arcuate gripping portions are spaced apart and a distal position in which the first and second engaging portions of the first and second arms are cammed against the elongate tubular member such that the first and second arcuate gripping portions are in close cooperative alignment, the first and second engaging portions being coplanar with remaining portions of the respective first and second arms.

14. The surgical grasping instrument according to claim 13, wherein the first and second arcuate gripping portions are semi-cylindrical.

15. The surgical grasping instrument according to claim 13, wherein the first and second arcuate gripping portions include teeth extending radially inward.

16. The surgical grasping instrument according to claim 13, wherein the living hinge and the first and second jaws are integrally formed.

17. The surgical grasping instrument according to claim 13, wherein concavities of the first and second arcuate gripping portions of the respective first and second jaws face each other when the elongate tubular member is in the proximal position.

\* \* \* \* \*